United States Patent [19]

McEwen

[11] Patent Number: 4,770,175

[45] Date of Patent: Sep. 13, 1988

[54] OCCLUSIVE CUFF

[75] Inventor: James A. McEwen, Richmond, Canada

[73] Assignee: Western Clinical Engineering Ltd., Vancouver, Canada

[21] Appl. No.: 921,461

[22] Filed: Oct. 22, 1986

[51] Int. Cl.[4] .......................... A61B 5/02; A61B 17/12
[52] U.S. Cl. .................................... 128/327; 128/679; 128/686
[58] Field of Search ............... 128/327, 679, 686, 672, 128/677

[56] References Cited

U.S. PATENT DOCUMENTS

| | | | |
|---|---|---|---|
| 2,031,870 | 2/1936 | Vertuno | 128/327 |
| 2,468,133 | 4/1949 | Sullivan | 128/327 |
| 3,095,873 | 3/1961 | Edmunds | 128/2.05 |
| 3,504,675 | 4/1970 | Bishop | 128/327 |
| 3,570,495 | 3/1971 | Wright | 128/327 |
| 3,587,584 | 6/1971 | Keller | 128/327 |
| 3,633,567 | 1/1972 | Sarnoff | 128/2.05 C |
| 3,670,735 | 6/1972 | Hazlewood | 128/327 |
| 3,699,945 | 10/1972 | Hanafin | 128/2.05 C |
| 3,756,239 | 9/1973 | Smythe | 128/327 |
| 3,765,405 | 10/1973 | Natkanski | 128/2.05 C |
| 3,812,844 | 5/1974 | Sokol | 128/2.05 C |
| 4,243,039 | 1/1981 | Aginsky | 128/327 |
| 4,308,871 | 1/1982 | Shouda | 128/686 |
| 4,331,155 | 5/1982 | Sacks | 128/686 |
| 4,399,809 | 8/1983 | Baro et al. | 128/346 |
| 4,437,470 | 3/1984 | Prost | 128/679 |
| 4,469,099 | 9/1984 | McEwen | 128/327 |
| 4,479,494 | 10/1984 | McEwen | 128/327 |
| 4,605,010 | 8/1986 | McEwen | 128/686 |

OTHER PUBLICATIONS

J. A. McEwen and R. W. McGraw, "An Adaptive Tourniquet for Improved Safety in Surgery", IEEE Trans. Bio-Med. Eng., vol. BME-29, 1982, pp. 122-128.

J. A. McEwen and G. F. Auchinleck, "Advances in Surgical Tourniquets," J. A. O. R. N., vol. 36, 1982, pp. 889-896.

J. A. Shaw and D. G. Murray, "The Relationship Between Tourniquet Pressure and . . . ", J. Bone & Joint Surg., vol. 64-A, 1982, pp. 1148-1152.

A. C. McLaren and C. H. Rorabeck, "The Pressure Distribution Under Tourniquets," J. Bone & Joint Surg., vol. 67-A, 1985, pp. 433-438.

R. J. Newman and A. Muirhead, "A Safe and Effective Low Pressure Tourniquet," J. Bone Joint Surg., vol. 68-B, 1986, pp. 625-628.

J. A. Shaw, W. W. Dernuth and A. W. Gillespy, "Guidelines for the Use of Digital Tourniquets . . . ", J. B. J. S., vol. 67-A, 1985, pp. 1086-1090.

J. D. Lubahn, J. Koeneman and K. Kosar, "The Digital Tourniquet: How Safe is It?" J. Hand Surg., vol. 10-A, 1985, pp. 664-669.

*Primary Examiner*—C. Fred Rosenbaum
*Assistant Examiner*—Gene B. Kartchner

[57] ABSTRACT

An occlusive cuff which is useful for safety occluding blood flow into the digit of a human subject distal to the cuff for the duration of a surgical procedure. The cuff comprises: an inflatable, readily collapsible tube formed of thin, flexible and substantially inextensible material wherein the ratio of the tube width to digit circumference is substantially smaller than the fixed ratio of tube width to digit circumference specified for a sphygmomanometer cuff which would accurately estimate blood pressure in the digit; means for securing the tube around substantially all of a portion of the digit; pressurizing means for pressurizing the tube; pressure relief means for depressurizing the tube; pressure sensing means for producing a cuff pressure output signal representative of the pressure to which the tube is pressurized; occlusion pressure selection means for selecting remotely the minimum constant pressure to which the tube should be pressurized to safety occlude blood flow into the digit distal to the cuff; pressure regulator means responsive to the cuff pressure output signal for selectably activating the pressurizing means and the pressure relief means to maintain the cuff pressure near the selected pressure over a time period suitably long for the performance of a surgical procedure.

13 Claims, 8 Drawing Sheets

OCCLUSIVE CUFF

FIELD OF THE INVENTION

This invention pertains to cuffs for occluding and controlling blood flow into a portion of a human or animal limb. The invention particularly pertains to a cuff useful in surgery for occluding blood flow into a portion of a limb or extremity as small as a single isolated digit, i.e. a finger, thumb or toe, which does not obstruct the surgical site, which includes means for selecting remotely the minimum constant pressure that should occlude blood flow safely and reliably in a particular limb of a normal subject encircled by a cuff chosen by a surgeon, and which functions as one element of an occlusive cuff system capable of accurately establishing and maintaining the pressure in the chosen cuff near the selected pressure for the duration of a surgical procedure.

BACKGROUND OF THE INVENTION

It is well known to use an inflatable cuff to control blood flow into a subject's limb for a brief period in order to estimate the subject's blood pressure, and to occlude blood flow into a limb for an extended period to provide a bloodless surgical field in the portion of the limb distal to the cuff. When employed to provide a bloodless surgical field, occlusive cuffs constitute one element of a surgical tourniquet system (hereinafter called a "tourniquet"). Tourniquets typically include the following basic elements: a source of pressurized gas, an inflatable cuff for encircling a limb at a selected location, and a pressure-regulating mechanism for controlling and maintaining the pressure of gas in the inflatable cuff, and thus the pressure applied by the cuff to the limb which the cuff encircles.

The recent advent of electronic tourniquets which employ digital technology in the regulation of pressure has led to significant improvements in the safety and accuracy of surgical procedures performed with an occlusive cuff applied proximally on a limb portion. These systems allow the surgeon to safely maintain a constant pressure on the limb which he estimates to be near the minimum required to safely occlude blood flow into the limb ("limb occlusion pressure"). However, similar improvements have yet to be largely realized in surgery of the isolated digit, i.e. in surgery of the finger or toe where such surgery is performed in conjunction with a tight band applied proximally on the digit to occlude blood flow into the digit. This lack of improvement in prior-art devices and techniques has persisted, despite an increasing frequency of surgery on the isolated digit due to reduced anesthetic risk and reduced complexity in comparison to alternate procedures involving anesthetizing a complete limb or the entire patient. Procedures involving surgery of the isolated digit at present include: suturing of lacerations, dry-field explorations for foreign bodies, open reductions of fractures, repairs of tendons, incisions and drainage of infected pulp spaces, and fusions of arthritic proximal interphalangeal and distal interphalangeal joints. At present, for example, it is estimated that more than 250,000 surgical procedures may be performed annually on isolated digits by orthopedic, plastic and trauma surgeons.

For surgery of the isolated digit, occlusion of blood flow is typically achieved by a 0.25-inch latex rubber tube known as a Penrose drain which is drawn tightly around the base of the proximal phalanx and secured with an hemostat, or by the use of a Penrose drain in the fashion of a miniature Esmarch bandage, or by the use of a finger from a surgical glove that is opened at the tip and rolled onto the finger from the distal to proximal end in order to exsanguinate the digit and leave a tight band at the base of the proximal phalanx. Some specific complications associated with these prior-art devices have been reported, and it has been suggested that the actual complication rate is much higher than the incidence of case reports in the literature. The devices which are commonly used for occluding blood flow into the digit have a number of problems and hazards associated with them. First, the actual pressure exerted on the digit may vary widely among surgeons having different application techniques, and among digits of differing circumferences, and may be considerably higher or lower than the minimum pressure required to occlude blood flow into the digit ("digit occlusion pressure"). Both excessively high pressures and excessively low pressures may be hazardous. One recent study found that occlusive pressures generated by rolled surgical gloves ranged from 113 to 363 mmHg, while pressures generated by Penrose drains exceeded 800 mmHg. Another recent study showed that the pressure beneath a 0.25-inch Penrose drain used as an occlusive band varied between 100 mmHg and 650 mmHg, and that the pressure generated beneath a rolled glove finger varied from 120 mmHg to more than 1000 mmHg.

A second disadvantage of common techniques for occluding blood flow into digits is that the pressure in the occluding band cannot be adjusted accurately or reliably by the surgeon intra-operatively; the inability to increase pressure intra-operatively may promote the use of techniques which routinely generate higher pressures than required in many instances.

A third disadvantage of commonly used techniques for occluding blood flow into digits is that the surgeon cannot release and re-establish occlusive pressure readily if desired during a procedure. This may adversely affect the nature and quality of some surgical procedures, because the surgeon cannot easily release pressure, evaluate the effect of blood flowing into the surgical site, and then re-establish a bloodless field in order to continue with the procedure.

A final disadvantage is that current methods do not permit the surgeon to monitor the pressure actually applied to the digit, so that the surgeon can relate hazards, incidents and unexpected clinical outcomes to applied pressures, and thus take appropriate remedial action if warranted during subsequent procedures.

A prior-art pneumatic cuff for use on digits has been described in the literature (see C. P. Tountas, "A disposable pneumatic digital tourniquet," J. Hand. Surg. Vol. 11A, 1986, pp. 600–601), although this prior-art cuff is not in widespread use. The prior-art pneumatic device consists of a mini-bladder held about a digit with hook and pile material, and is connected to a syringe, whose air can be compressed and held by a spring housing. Two markings are given on the barrel of the syringe so that the plunger may be depressed to either of these two markings to compress air in an attempt to generate one of two arbitrary pneumatic pressures in the cuff as it encircles a digit. This prior-art device has significant limitations which restrict its utility and which prevent significant improvements in safety from being achieved clinically. First, it has been found in work which led to the present invention that the minimum occlusion pressure for digits, i.e. the digit occlusion pressure, varies according to the digit circumference for a cuff of a specified width and design; with the prior-art pneumatic cuff the digit occlusion pressure will vary widely as a function of digit circumference, and the cuff does not allow for estimation of the digit occlusion pressure when the cuff encircles a particular digit. The pressure established by depressing the barrel of the syringe in the prior-art pneumatic cuff system will be rather arbitrary and will likely be significantly higher or lower than the digit occlusion pressure. Second, the degree to which the air in the prior-art pneumatic system must be compressed by depressing the plunger of the syringe in order to achieve some arbitrary pressure depends upon the snugness with which the cuff was initially applied to the digit and also depends upon the extent to which segments of the mini-bladder of the cuff overlap as they encircle the digit. Third, the prior-art pneumatic cuff has a significant discontinuity at the cuff/digit interface caused by overlapping of thick cuff segments, which results in variations in applied pressure over a localized area. Fourth, the prior-art pneumatic cuff has only one means of securing the cuff around a digit, which may be hazardous at high pressures in that the event that the securing means becomes ineffective. Fifth, the prior-art pneumatic cuff will remain pressurized to a constant pressure only if there are no leaks in the system. In practice leaks occur, especially at the connection between the syringe and the cuff. The prior-art pneumatic cuff is not able to compensate for such leaks, and so in the presence of leaks the pressure will decrease to a hazardous level and permit blood to flow into the surgical site. The prior-art pneumatic cuff provides for no monitoring of the actual pressure in the cuff by pressure sensing means. Also, the prior-art pneumatic cuff allows for no precise regulation of pressure to maintain the pressure in the cuff near a desired pressure for the duration of a surgical procedure, or to allow for controlled blood flow at certain times during the surgical procedure if desired by the surgeon, or to allow for adaptation of the cuff pressure in response to changes in the patient's blood pressure. Finally, the prior-art pneumatic cuff contains no alarm means to warn the surgeon in the event of a hazard such as loss of pressure.

One of the limitations of the prior-art pneumatic cuff for digits described above illustrates a problem common to all prior-art pneumatic cuffs which are intended for use on limbs. At present, a variety of pneumatic cuffs of different designs, including differing widths, circumferences, shapes and materials, are manufactured for use on limbs as occlusive cuffs. These cuffs do not enable the surgeon to estimate reliably the minimum constant pressure normally required to safely occlude blood flow over a time period suitably long for the performance of a surgical procedure in a limb encircled by a particular cuff which he chooses. Instead, many surgeons presently set cuff pressures rather arbitrarily, without adequately taking into account the circumference of the patient's limb at the cuff site and pertinent characteristics of the design of the specific cuff employed, including the width of the cuff. This can be hazardous because the minimum constant pressure which must be established in a cuff encircling a portion of a limb to safely occlude blood flow distal to the cuff for the duration of a surgical procedure is dependent on variables including the circumference of the limb at the cuff site and specific characteristics of the design of the cuff employed, especially with respect to its width and shape, as well as being dependent on significant fluctuations in systolic blood pressure which normally occur in anesthetized subjects over the time period of a surgical procedure. Methods have been described in the prior art to assist surgeons in estimating limb occlusion pressures as a function of limb circumferences. However, these methods do not take into account the significant differences in characteristics among different cuffs, and require the surgeon to measure the circumference of a limb at the cuff site, and then to refer to a separate graph for estimating the limb occlusion pressure; these methods are impractical and error-prone due to the difficulty of accurately measuring the circumference of a limb at the prospective cuff site prior to cuff application and surgery, due to wide variations in the snugness of initial cuff application and thus the effective cuff circumference, and due to errors which may arise in interpolating using a separate graph to estimate occlusive pressure. Also, most significantly, the separate graphs on which these methods are based may have been obtained using cuffs of much different design than the cuff to be employed by the surgeon, and hence the pressure/circumference relationship employed may not be accurate for that cuff. Also, the graphs on which these methods are based may have been based on cadaver studies or studies of a small number of subjects not similar to the patient undergoing surgery.

The applicant is aware of the following United States patents which are more or less relevant to the subject matter of the applicant's invention.

| | | | | |
|---|---|---|---|---|
| 4,605,010 | 8/1986 | McEwen | | 128/686 |
| 4,479,494 | 10/1984 | McEwen | 128/327 | 128/682 |
| 4,469,099 | 9/1984 | McEwen | 128/327 | 128/682 |
| 4,308,871 | 1/1982 | Shouda | | 128/686 |
| 3,812,844 | 5/1974 | Sokol | 128/2.05G, | 128/2.05C |
| 3,765,405 | 10/1973 | Natkanski | | 128/2.05C |
| 3,756,239 | 9/1973 | Smythe | 128/327, | 128/2.05C |
| 3,699,945 | 10/1972 | Hanafin | 128/2.05C, | 128/327 |
| 3,670,735 | 6/1972 | Hazlewood | | 128/327 |
| 3,633,567 | 1/1972 | Sarnoff | 128/2.05C, | 128/327 |
| 3,587,584 | 6/1971 | Keller | | 128/327 |
| 3,570,495 | 3/1971 | Wright | | 128/327 |
| 3,504,675 | 4/1970 | Bishop | | 128/327 |
| 3,095,873 | 3/1961 | Edmunds | | 128/2.05 |
| 2,468,133 | 4/1949 | Sullivan | | 128/327 |
| 2,031,870 | 2/1936 | Vertuno | | 128/327 |

The applicant is also aware of the following published reference which are more or less relevant to the subject matter of the applicant's invention.

J. A. McEwen and R. W. McGraw, "An adaptive tourniquet for improved safety in surgery." IEEE Transactions in Bio-Medical Engineering, Vol. BME-29, February 1982, 122–128.

J. A. McEwen and G. F. Auchinleck, "Advances in surgical tourniquets," J. Assn. Operating Room Nurses, Vol. 36, 1982, pp. 889–896.

J. A. Shaw and D. G. Murray, "The relationship between tourniquet pressure and underlying soft-tissue pressure in the thigh." The Journal of Bone Surgery, Vol. 64-A, 1982, pp. 1148–1152.

A. C. McLaren and C. H. Rorabeck, "The pressure distribution under tourniquets." The Journal of Bone and Joint Surgery, Vol. 67-A, 1985, pp. 433–438.

R. J. Newman and A. Muirhead, "A safe and effective low pressure tourniquet." Journal of Bone and Joint Surgery, Vol. 68-B, 1986, 99. 625–628.

J. A. Shaw, W. W. Demuth, and A. W. Gillespy, "Guidelines for the use of digital tourniquets based on physiological pressure measurements." The Journal of Bone and Joint Surgery, Vol. 67-A, 1985, pp. 1086-1090.

J. D. Lubahn, J. Koeneman and K. Kosar, "The digital tourniquet: How safe is it?" J. Hand Surg., Vol. 10A, 1985, pp. 664-669.

SUMMARY OF THE INVENTION

The invention is directed to an occlusive cuff system for safely occluding blood flow into a portion of a limb as small as a single isolated digit in order to facilitate surgery in the limb portion, comprising: an inflatable tube having a collapsed width which does not obstruct the surgical site and having a length sufficient for encircling the limb at a selected location; means for securing the tube so that the tube substantially encircles the limb at a selected location without overlapping on itself; means for stiffening the outer surface of the tube to help direct inflation inwardly when the tube is inflated; means for selecting remotely the minimum constant pressure normally required to inflate the tube of the cuff in order to occlude blood flow when the tube encircles a specific limb; means for supplying gas near the selected minimum constant pressure to the tube of the cuff secured around the limb; and means for producing an indication representative of the pressure of gas in the inflated tube of the cuff for the duration of a surgical procedure. Means are provided to enable the inflatable tube to be used for estimating the maximum pressure applied by any pneumatic or non-pneumatic occlusive band to the tissue which it encircles, and means are provided to employ the maximum pressure thus estimated in the regulation of the pressure applied by the occlusive band.

The tube of the cuff may consist of thin, flexible and substantially inextensible material having a length sufficient to encircle at a selected location a limb. The ratio of tube width to the circumference of the limb portion being encircled may be substantially different than the fixed ratio of tube width to limb circumference normally required of a sphygmomanometer cuff for accurate estimation of blood pressure in the same limb. A retaining strap may be included to retain the tube in position around the limb and to help direct inflation inwardly when the tube is inflated.

Means may be included to secure the tube around the limb independently of the means to secure the retaining strap around the tube so that the tube remains encircling the limb if either one of the two securing means become ineffective.

The means for selecting remotely the minimum constant pressure to which the cuff should be inflated as it encircles a digit in order to safely occlude blood flow may comprise pressure graduations marked on a surface of the cuff. The pressure graduations may estimate the minimum constant pressure which has been found to safely occlude blood flow when a cuff of the same design and dimensions snugly encircles a limb of similar circumference in a subject having similar blood pressure. The pressure graduations may be marked on cuffs which, when encircling the limb, have width to circumference ratios that may be significantly smaller or larger than the standard ratio of cuffs recommended for accurate estimation of blood pressure in the same limb. Means may be provided to enable selection of pressure remotely by digital computing means to facilitate the automatic adaptation and regulation of pressure.

Pressurizing means for supplying gas near the selected pressure to the tube of the cuff for the duration of a surgical procedure may consist of a combination of pressure generator, generated pressure sensor, and digital processor connected together.

Cuff pressure sensing means for producing an indication representative of the pressure of the gas in the tube of the cuff may consist of an electronic pressure sensor and may include means for producing a cuff blockage alarm when the difference between the pressure of the pressurized gas supplied to one end of the tube and the pressure of gas sensed at the other end of the tube exceeds a predetermined limit.

The inflatable, inextensible tube may be coupled at one end to cuff pressure sensing means and coupled at the other end to the pressurizing means such that there must be an opening in the tube around substantially all of the circumference of the limb for the pressure sensing means to indicate the pressure of gas supplied by the pressurizing means.

In a different configuration, the occlusive cuff system of the invention may be employed to estimate and monitor the maximum pressure applied by any pneumatic or non-pneumatic occlusive band to the limb encircled by the occlusive band. In this configuration, a tube having a width much smaller than the width of the occlusive band is positioned longitudinally along the limb, between the limb surface and the occlusive band, and includes: means for causing fluid at a variable pressure to be coupled to one end of the tube, means for producing a signal representative of the pressure of the fluid supplied to the end of the tube; and means for increasing the pressure of the fluid supplied from a low pressure to a level beyond which the pressure does not increase because the tube opens at that pressure and allows fluid to escape between the limb and occlusive band. Means may be included which are responsive to the signal representative of the pressure at which the tube opens, for regulating the pressure applied by the occlusive band to the limb which the band encircles in order to maintain the pressure applied by the occlusive band near a selected level.

General Characteristics and Attributes of the Invention

The occlusive cuff of the invention enables occlusive pressure to be established and maintained more safely, more accurately and more reliably on human digits than prior-art cuffs. When occlusive cuffs are applied proximally on limbs, it is known that the limb occlusion pressure at a particular instant, i.e. the minimum pressure required to occlude blood flow into the limb distal to the cuff, is a function of variables including cuff width, shape and design, limb circumference, and the patient's ongoing systolic pressure. In work leading to the present invention, it was determined that the occlusion pressure for human digits was similarly affected by the same variables that affect the limb occlusion pressure. The present invention assists the surgeon in employing the lowest practicable pressure on the digit by assisting him in (a) choosing the widest cuff which does not interfere with the specific surgical procedure to be performed, (b) selecting the lowest constant pressure to which the chosen cuff should normally be inflated to occlude blood flow in a specific digit of a normotensive patient over a time period suitably long for the performance of a surgical procedure, in order to minimize the applied pressure and thus the hazard to the patient, and (c) employing the chosen cuff with pressure-regulating means to reliably establish and maintain the pressure in the cuff near the selected pressure for the duration of a surgical procedure.

The cuff of the invention permits the use of consistently lower and safer pressures for occluding blood flow for surgery of the isolated digit. Results of laboratory investigations indicate that it should be possible to employ occlusive pressures as much as 75% below that which might be generated by a prior-art Penrose drain, and as much as 60% below the pressure that might be generated by the use of a rolled glove finger as described in the prior art. In addition; it is possible for the surgeon to monitor and control the applied pressure through the use of the cuff of the invention in conjunction with a digital tourniquet (such as the Model ATS 1000 Automatic Tourniquet System, Aspen Labs, Littleton, Colo.) to automatically regulate the pressure in the cuff. The cuff of the invention may be used in orthopedic, plastic and trauma surgery. The cost implications associated with using the present invention are small if a digital tourniquet is already available.

The cuff of the invention, with dimensions increased proportionately, may be used to occlude blood flow into portions of limbs larger than digits. For this usage, a cuff having a much greater width which still does not obstruct a surgical site distal to the cuff may be employed, incorporating means for selecting remotely the minimum constant pressure to which the cuff should be inflated for safely and reliably occluding blood flow into the limb of a normotensive subject distal to the cuff over a time period suitably long for the performance of a surgical procedure.

The means for remotely selecting the occlusion pressure may comprise visible graduated pressure markings on the cuffs, or the means may comprise electrical circuitry so that the occlusion pressure can be selected remotely by digital computing means. Thus an attribute of the present invention is that it enables remote selection of the minimum constant pressure for safely and reliably occluding blood flow into the limb or digit distal to a chosen cuff which encircles the limb or digit of a normotensive patient at a selected location.

The cuff of the invention may also be employed more generally to estimate, monitor, and regulate the pressure applied by any pneumatic or non-pneumatic occlusive band to any segment of a human or animal limb. This is accomplished by choosing a cuff having a tube width which is very small in relationship to an occlusive band which encircles a limb. The collapsed tube of the invention is placed longitudinally between the occlusive band and the limb beneath the band, and is connected to a pressurizing source. The pressurizing source may be gradually increased from zero to a level which cannot be exceeded; that level is indicative of the maximum pressure exerted by the occlusive band on the limb which the cuff encircles.

Other attributes of the cuff of the invention which are significant include an inflatable tube which permits an operator or automated device to assure that there is a continuous passageway for gas from one end of the tube around the digit to the other end without obstruction during clinical usage, and a connector to secure the tube around substantially all of a digit or limb without the tube overlapping on itself; this helps reduce discontinuities at the cuff/tissue interface, and helps reduce non-uniform displacement and non-uniform pressurization of tissue. Finally, an important attribute of the cuff of the invention is that it is intended primarily for use as one component of an occlusive cuff system which also includes a commercially available digital tourniquet so that pressure in the cuff can be maintained accurately and reliably near a selected pressure for the duration of a surgical procedure.

Another general characteristic of the invention which is significant clinically concerns the wide range of cuff widths which can be employed. This facilitates the clinical use of a cuff having the greatest width which does not interfere with the surgical procedure, accompanied by pressure selection means such as pressure graduations marked on the cuffs which indicate the normal occlusion pressure when that cuff is encircles a specific digit or limb. In surgery, this permits the use of cuffs that are significantly narrower than the standard cuffs commonly employed for accurate blood pressure measurements. In other situations where the cuff may be located proximally on a limb and a surgical procedure is to be performed distally away from the cuff, it may be possible to use a wide cuff with dimensions which produce a cuff width to limb circumference ratio significantly larger than the fixed ratio of 0.4 accepted in the prior art for accurately estimating blood pressure at a particular instant; in such surgical situations, obstruction of the surgical site is not a significant issue because it is distant from the cuff, and the use of a wide cuff on a limb with resultant width to circumference ratio larger than 0.4 may permit the use of much lower pressures than would otherwise be utilized. Because injuries to the tissue beneath the cuff are thought to be proportional to the pressure applied by the cuff, the use of wider cuffs and lower pressures where possible may reduce the probability of such injuries. The use of the cuff of the invention with a width to circumference ratio greater than blood pressure cuffs is facilitated by the inclusion of cuff pressure selection means consisting of pressure graduations or electrical circuitry to enable remote selection of the minimum constant pressure to which the cuff should be inflated in order to occlude blood flow into the portion of the limb distal to the cuff, in a patient having blood pressure and limb shape similar to those of test subjects used to determine the pressure graduations or to calibrate the electrical circuitry.

BRIEF DESCRIPTION OF THE DRAWINGS

A specific embodiment of this invention has been chosen for purposes of illustration and description wherein.

DESCRIPTION OF THE SPECIFIC EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 3:
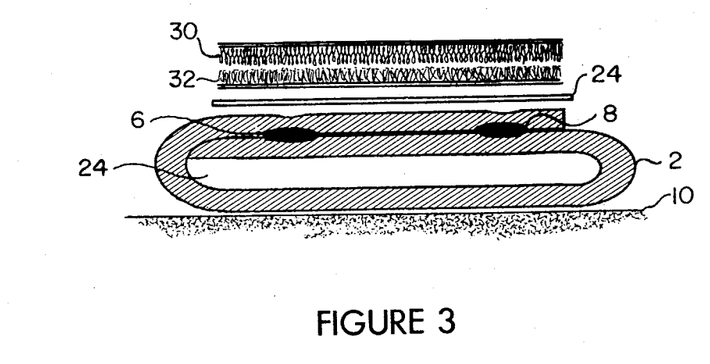
FIG. 3 is a sectional view taken along line 3—3 of FIG. 2.
Figure 4:
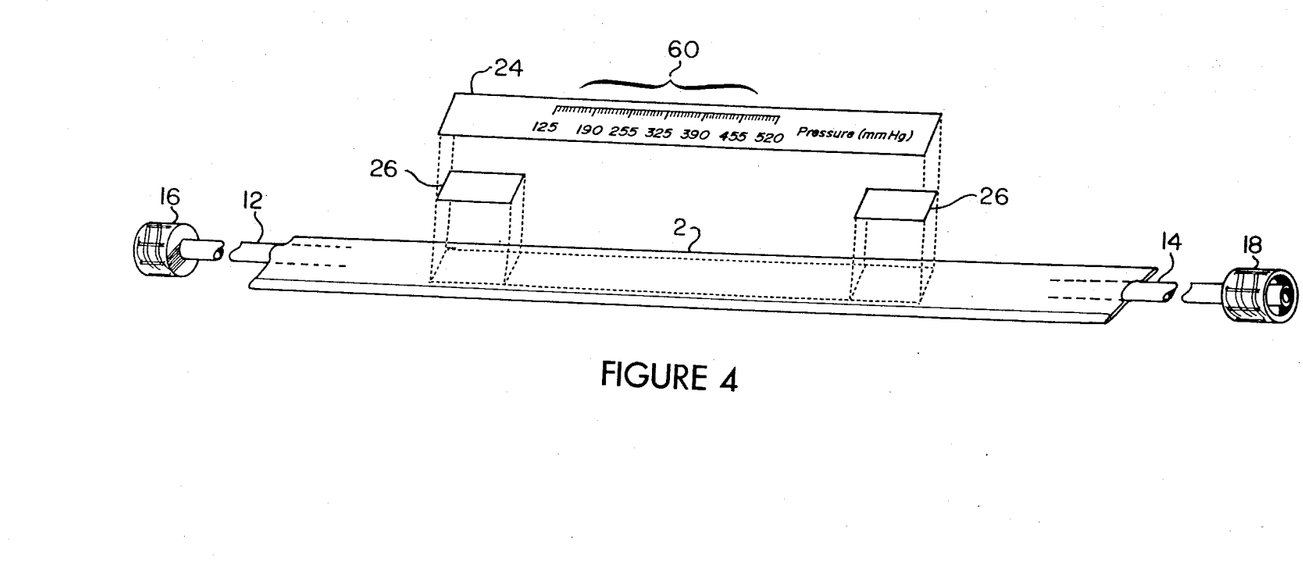
FIG. 4 is an exploded view of the inflatable tube in the cuff of FIG. 1.

The cuff of this invention, as can be seen in FIG. 4, includes an inflatable tube 2 formed by first folding and sealing a rectangular sheet of thin, flexible material which is substantially inextensible at pressures up to about 500 mmHg. To form tube 2 having dimensions suitable for use on human digits, a rectangular sheet of material having a length of about 20 cm and having a width which will produce a tube of the desired width when collapsed is folded and bonded at seals 6 and 8, which can be seen in FIG. 3, so that the sealed surface is an outer surface which is not normally in contact with digit 10 when tube 2 encircles digit 10. In the cuff of the invention, tubes having collapsed widths of 8.0, 10.0, 12.5 and 15.5 mm were fabricated from Herculite TM 10W material (Herculite Products Inc., New York, N.Y. 10010) which contains an embedded inextensible mesh, and tubes having collapsed widths of 11.0 and 15.0 mm were fabricated from 300-gauge soft transparent vinyl. The vinyl tubes having widths of 11.0 and 15.0 mm were conveniently formed from in part from vinyl hospital identification bracelets (2-line and 3-line Ident-a-Band TM bracelets, Hollister Incorporated, Libertyville, Ill. 60048), which were found to be folded and sealed in a manner similar to that described above, and which were found to be capable of withstanding pressurization to more than 500 mmHg.

Figure 1:
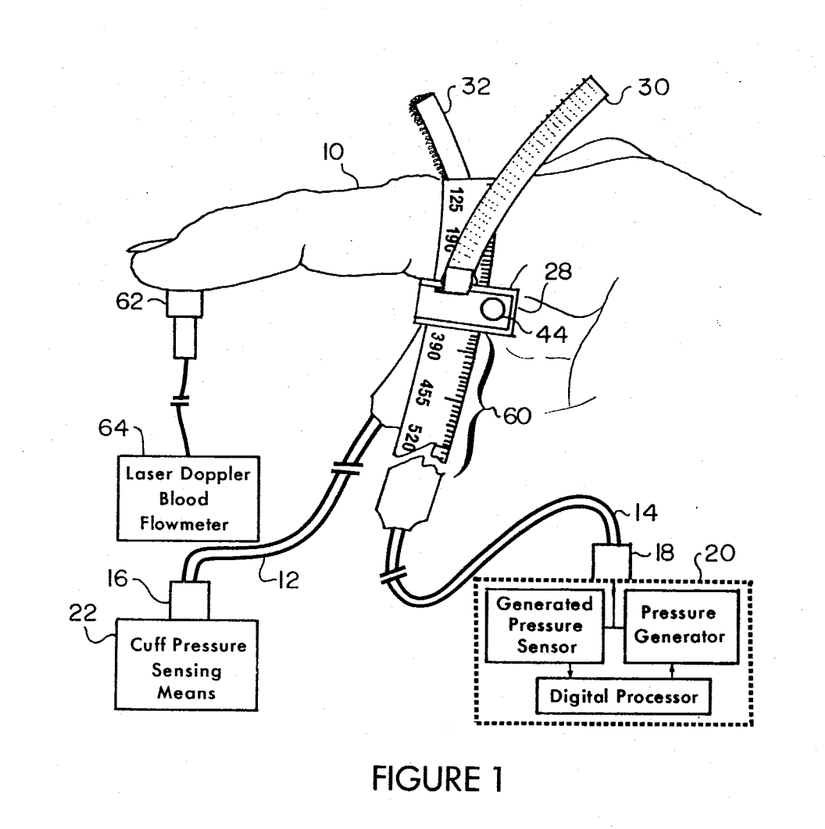
FIG. 1. is a perspective view of the cuff of this invention applied to the digit of a human subject.
Figure 2:
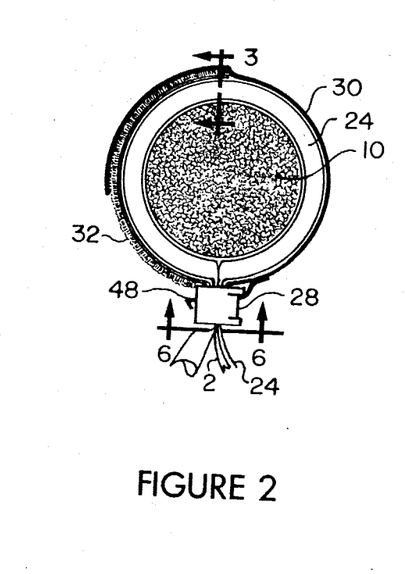
FIG. 2 is a cross-sectional view of the cuff of FIG. 1 encircling the digit.

As can be seen most clearly in FIG. 4 and FIG. 1, hoses 12 and 14 are bonded to the ends of tube 2 and to Luer-lock adapters 16 and 18 to enable attachment of hoses 12 and 14 to pressurizing means 20 and pressure sensing means 22 so as to provide a gas-tight conduit or passageway 24 for pressurized gas to pass from pressurizing means 20 through the entire length of tube 2 to pressure sensing means 22.

Stiffening strip 24 may be attached to the top surface of tube 2 with double-sided adhesive tape 26. Stiffening strip 24 may be formed of a transparent, flexible, inextensible material such as polyester, Mylar TM or celluloid, and is attached to tube 2 so as to help direct inflation inwardly when tube 2 is secured snugly around a an extremity at a selected location and pressurized.

Figure 5:
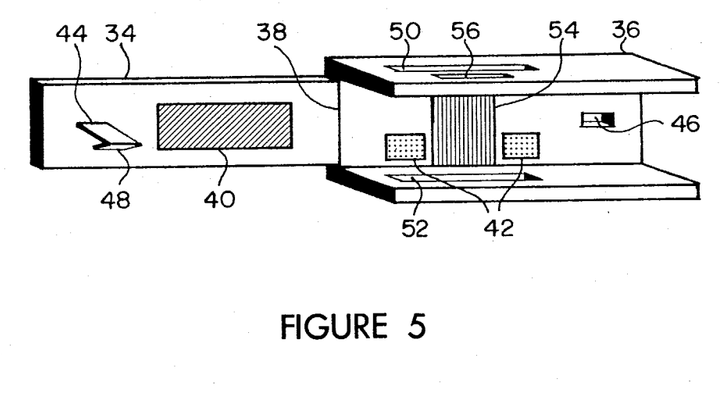
FIG. 5 is an enlarged perspective view of the cuff connector shown in FIG. 1 to better illustrate the tube-securing means and the retaining strap-securing means.
Figure 6:
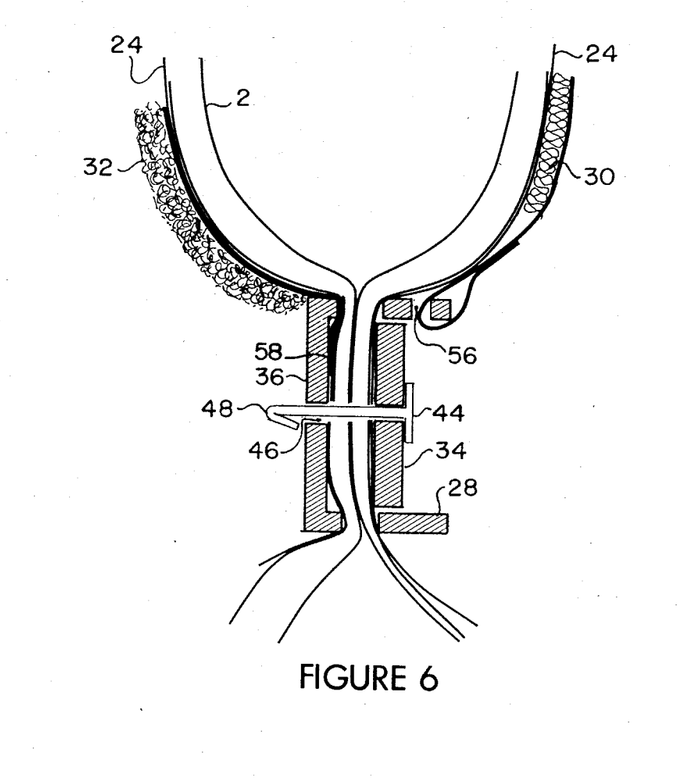
FIG. 6 is a sectional view taken along line 6—6 of FIG. 2 to better illustrate the relative location of cuff components at the cuff connector.

Cuff connector 28 which is shown in detail in FIG. 5 provides tube-securing means for securing tube 2 snugly around substantially all of the circumference of digit 10 without allowing tube 2 to overlap on itself around the digit, and provides means for independently securing a retaining strap comprised of two complementary strips 30 and 32 of hook and pile material around the outer surface of tube 2 such that tube 2 remains snugly encircling digit 10 in the event that the tube-securing means becomes ineffective. Cuff connector 28 is formed of a plastic material capable of repeated flexing, such as the polypropylene strips commonly produced for use as plastic hinges. As can be seen in FIG. 5, cuff connector 28 is formed from a narrow strip of polypropylene having sides 34 and and 36 separated by hinge 38 so as to allow side 34 to be folded toward side 36 to firmly engage two sections of tube 2. Irregular surface 40 is included on side 34 to help firmly engage a section of tube 2. Side 36 includes adhesive strips 42 for adhering to one side of tube 2 in order to retain that side of tube 2 in a fixed position with respect to cuff connector 28, so that only the other side of tube 2 must be pulled through cuff connector 28 to tighten tube 2 around digit 10. Side 34 includes fastener 44 attached to it so that fastener 44 passes through hole 46 on side 36 to engage and hold sides 36 and 34 against sections of tube 2 with sufficient force to prevent the engaged sections of tube 2 from slipping when tube 2 is snugly secured around digit 10 and pressurized to a maximum pressure of about 500 mmHg. As indicated more clearly in the sectional view shown in FIG. 6, fastener 44 is formed of a resilient material such as brass or plastic which is folded at tip 49 in a manner such that folded tip 48 spreads apart after being pushed through hole 46, and such that folded tip 48 must be pinched together manually in order to release side 34 and thus permit tube 2 to be loosened and removed easily from digit 10.

As can be seen in FIG. 5, cuff connector 28 includes guide slots 50 and 52, each having a length slightly greater than the collapsed width of tube 2, to facilitate alignment of the engaged sections of tube 2. The width of guide slots 50 and 52 is slightly greater than twice the thickness of tube 2, to facilitate the passage of pressurized gas. Cuff connector 28 also includes groove 54 to help assure a passageway for pressurized gas to pass through the engaged sections of tube 2.

Cuff connector 28 provides means for attaching a retaining strap which functions independently of the tube-securing means. The primary function of the retaining strap is to wrap snugly around the outer surface of the collapsed tube as it encircles digit 10 at a selected location so as to help direct inflation inwardly when tube 2 is pressurized. The retaining strap comprises complementary strips 30 and 32 of hook and pile positioned so that they can be wrapped around the outer surface of tube 2 and fastened together. As can be seen more clearly in FIG. 6, strip 30 of hook material is fastened to cuff connector 28 by looping it through anchoring slot 56, and the strip 32 of pile material is attached to side 36 of cuff connector 28 by adhesive 58. This implementation of retaining strap-securing means assures that the retaining strap is secured around digit 10 independently of the tube-securing means such that tube 2 remains snugly encircling the extremity if either the tub-esecuring means or the strap-securing means becomes ineffective.

Figure 7:
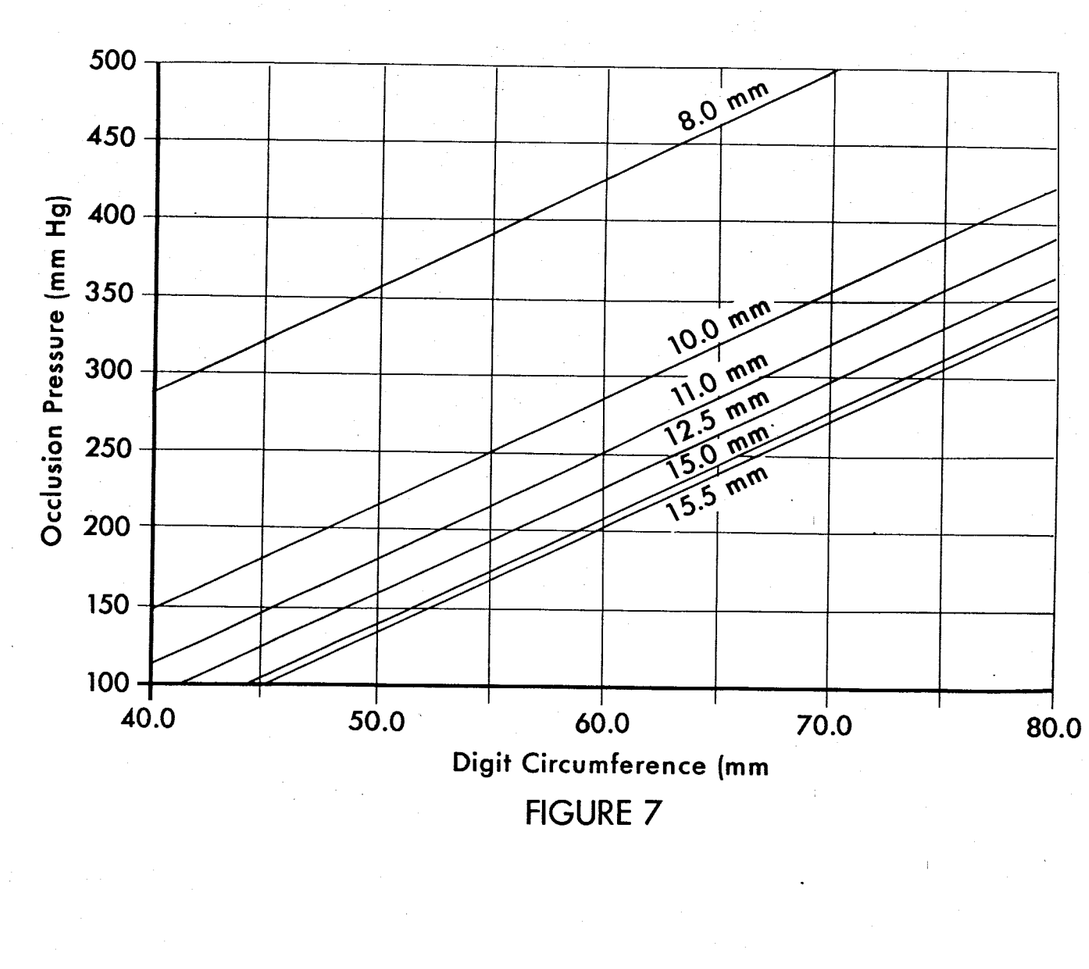
FIG. 7 is a graph used to determine the pressure graduations marked on cuffs having tubes of different widths.

As can be seen in FIG. 1 and FIG. 4, the cuff of the invention includes pressure graduations 60 marked on tube 2 or, if more convenient, on stiffening strip 24. The graduations 60 are marked on tube 2 or stiffening strip 24 such that the first graduation visible on the segment of tube 2 protruding below cuff connector 28 nearest to the outer edge of cuff connector 28 when the cuff is snugly secured around digit 10 indicates the minimum constant pressure to which that cuff should normally be inflated in order to safely and reliably occlude blood flow into the portion of digit 10 distal to the cuff over a time period suitably long for the performance of a surgical procedure. The pressure graduations 60 for cuffs of the invention having collapsed widths of 8.0, 10.0, 11.0, 12.5, 15.0 and 15.5 mm were derived from the corresponding curves shown in FIG. 7. The curves shown in FIG. 7 were developed as follows. First a large number of normotensive volunteers was identified and a cuff having the same structure and tube width as the cuff to be employed clinically was was applied to each of their digits. For each digit, with the cuff applied proximally on the digit as shown in FIG. 1, the probe 62 of a laser-doppler blood flowmeter 64 was attached to the tip of the digit 10. Pressure was slowly decreased from a high level which occluded blood flow to the first level at which the onset of blood flow into the digit could be detected. This test was repeated after a relaxation period and the average of the lowest pressures at which no blood flow could be detected was taken to be the digit occlusion pressure for that cuff and instantaneous digit. The circumference of the digit at the selected location, i.e. the middle of the cuff site, was measured, and the result was plotted. When data from all digits of the sample of all subjects had been collected and plotted, a linear curve was drawn to show minimum pressure as a function of cuff type and digit circumference, which occluded bloodflow into all digits tested. FIG. 7 shows the resultant lines for cuffs of structures as described above and of widths as marked beside the curves. Graduations derived from the relationships shown in FIG. 7 were marked at the appropriate positions on cuffs having tubes of corresponding widths. In deriving each of the pressure graduations 60, an additional increment of 50 mmHg was added to each value obtained from FIG. 7 to account for the maximum increase in systolic blood pressure which might normally occur in normotensive patients over a time period suitably long for the performance of a surgical procedure. Thus each one of the pressure graduations 60 is an estimate of the minimum constant pressure normally required in the cuff when the cuff is secured snugly around a non-hypertrophied and non-atrophied digit of predetermined circumference in a normotensive subject to occlude blood flow into the digit distal to the cuff over a time period suitably long for the performance of a surgical procedure. In the cuff of the invention, pressure graduations 60 were marked on tube 2 such that they would be visible to an operator, but alternatively electrical circuitry for remotely selecting a constant pressure to which the cuff should normally be inflated in order to safely and reliably occlude blood flow in the portion of digit 10 encircled by the cuff for the duration of sugery could be employed by adapting the technique for remotely determining cuff circumferences described in the inventor's U.S. Pat. No. 4,605,010. This would facilitate use of digital computing means for increasing or decreasing the selected pressure in response to increases or decreases in the blood pressure of the subject.

The capability of the cuff of the specific embodiment to enable remote selection of the best constant pressure for inflation of the cuff to occlude blood flow is clinically significant. The constant pressure thus selected may be further increased or adapted by the surgeon to account for intraoperative increase in the patient's systolic blood pressure or other abnormal conditions, but even the use of the selected constant pressure without adaptation will significantly increase the probability that a low pressure close to the optimal occlusion pressure for the duration of the surgical procedure will be employed. This characteristic of the cuff of the invention makes the cuff fundamentally different in cuffs employed in sphygmomanometer systems, where the fundamental goal is to employ a cuff with a fixed, standardized ratio of cuff width to limb circumference equal to 0.4, so that blood pressure in the limb at a particular instant will be estimated accurately.

To clinically use a cuff of the specific embodiment described above on a human digit, the operator first selects the widest of the available cuffs which does not interfere with the surgical procedure to be performed. The selected cuff is usually gas sterilized by a standard method which employs ethylene oxide. The retaining strap-securing means and tube-securing means of the selected cuff are released, and tube 2 is pulled through cuff connector 28 so that there is a sufficiently large loop of tube 2 for positioning loosely around digit 10 at the selected location, without allowing the tube 2 to contact digit 10 distal to the selected location. The side of tube 2 which is not affixed to cuff then pulled through alignment slots 50 and 52 of cuff connector 28 until tube 2 is in snug contact with digit 10 around substantially all of its circumference. Side 34 of cuff connector 28 is then folded onto side 36 until fastener 44 engages to secure the collapsed tube 2 around digit 10. Strips 30 and 32 of hook and pile material are then wrapped snugly around the outer side of the collapsed tube 2 and attached to each other to form an independent retaining strap. The portion of pressure graduations 60 on the segment of tube 2 protruding from cuff connector 28 is then observed. The graduation corresponding to the lowest pressure visible beneath cuff connector 28 is noted. This pressure corresponds to the lowest constant pressure normally required in a cuff of that width and design to safely and reliably occlude blood flow over a time period suitably long for the performance of a surgical procedure when the cuff snugly encircles a normal digit of that circumference in a normotensive subject. Luer-lock adapters 16 and 18 are connected to pressurizing means 20 and cuff pressure sensing means 22, as can be seen in FIG. 1. The digit 10 is exsanguinated conventionally, and pressurizing means 20 is set to supply gas at the pressure selected as described above, in order to occlude blood flow. In practice, an additional margin of about 50 mmHg may be added to the lowest visible pressure graduation to account for special conditions such as a hypertensive patient, an abnormal digit, or abnormally high intra-operative increases in systolic pressure. Once the cuff is inflated to the selected pressure, if anticipated, the surgical procedure can commence. If desired during the procedure, the operator can deliberately reduce or increase the pressure in the cuff by adjusting the selected pressure. At the end of the surgical procedure, the cuff is deflated, and the retaining strap-securing means and tube-securing means are released so that the tube can be loosened and the cuff removed from the digit.

Figure 8:
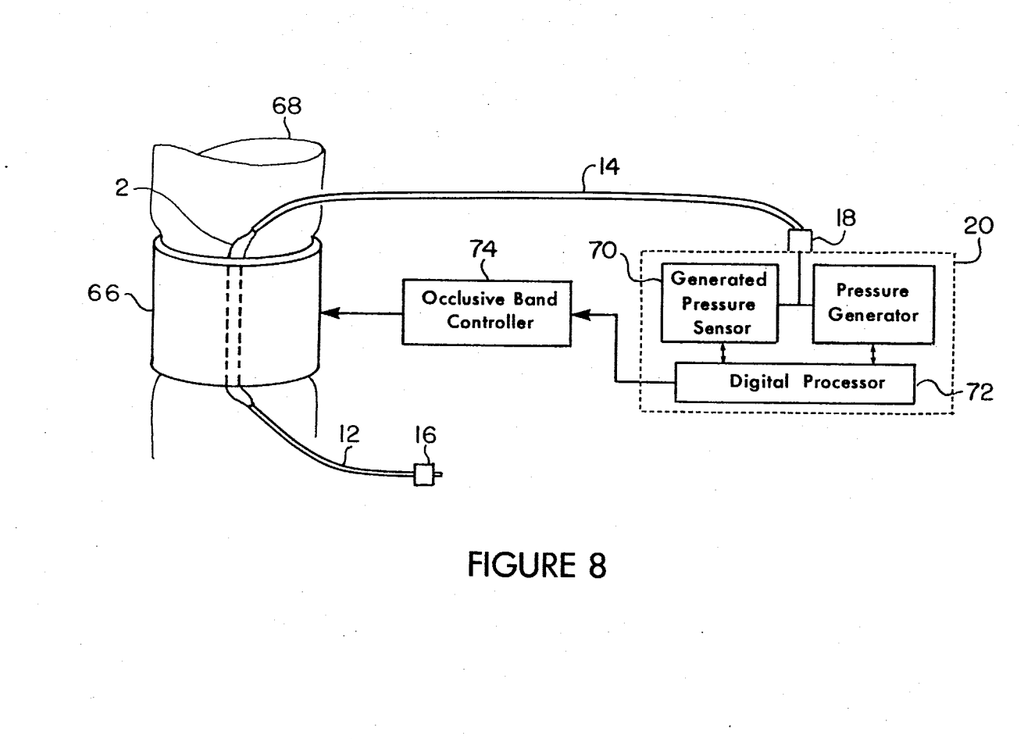
FIG. 8 is a block diagram showing the cuff of the invention employed to estimate the maximum pressure applied by any pneumatic or non-pneumatic occlusive band to a limb segment.

The cuff of the specific embodiment described above can be employed more generally to estimate, monitor and regulate the pressure applied by any pneumatic or non-pneumatic occlusive band to any segment of a human or animal limb, as illustrated in FIG. 8. To use the cuff of the invention as illustrated in FIG. 8, tube 2 is selected or fabricated such that its width is very small in relation to the width of the occlusive band 66, and its length is greater than the width of occlusive band 66. In constructing tube 2, care is taken to assure that the passageway 24 for gas is blocked completely when a low pressure is exerted by occlusive band 66 on limb segment 68. The distal end of hose 12 is left open to air. In operation, the pressurizing source 20 is employed to increase the pressure gradually from zero to a constant value which is reached when the pressure is sufficient to open passageway 24 and allow pressurized gas to pass through tube 2 between the occlusive band 66 and limb segment 68, and thus escape. The constant level of pressure which is reached in this manner is representative of the maximum pressure applied by occlusive band 66 to limb segment 68. As illustrated in FIG. 8, the pressure which is sensed by generated pressure sensor 70 is controlled and monitored by digital processor 72, so that determinations of the maximum constant pressure can be made repeatedly and so that the maximum constant pressure which is reached can be passed by digital processor 72 to occlusive band controller 74, to permit the pressure applied by occlusive band 66 to the limb segment 68 to be automatically and periodically adjusted near a desired level. This configuration of the cuff of the invention is advantageous for use in conjunction with any occlusive band applied to any portion of a human or animal limb because it can be employed with non-pneumatic and pneumatic occlusive bands, and because it accurately indicates the maximum pressure applied by the occlusive band to the limb beneath the band, and takes into account both the snugness of the initial application of the band to the limb and any subsequent changes in pressure controlled by occlusive band controller 74.

It is to be understood that the invention is not to be limited to the details herein given but may be modified within the scope of the appended claims.

I claim:

1. An occlusive cuff for safely occluding blood flow into a portion of a limb as small as a single, isolated digit to facilitate surgery on the limb portion, comprising in combination:
   (a) a pressurizable, substantially inextensible tube having a length sufficient for encircling a limb at a selected location, and having a width wherein the ratio of tube width to limb circumference at the selected location is substantially different than the ratio of bladder width to limb circumference required in a sphygmomanometer cuff for accurate estimation of blood pressure at the selected location;
   (b) means for snugly encircling the limb with the tube at the selected location in a manner that does not allow the tube to contact the limb distal to the selected location, and so that the tube contacts the limb around substantially all of its circumference without overlapping around the limb;
   (c) tube-securing means for securing the tube so that the tube remains snugly around the limb at the selected location while the tube is pressurized to a level sufficient to occlude blood flow in the limb encircled by the tube;
   (d) occlusion pressure selection means for selecting remotely the minimum constant pressure to which the tube should be pressurized to occlude blood flow in the limb, wherein the occlusion pressure selection means comprises pressure graduations marked on the tube so that a pressure graduation corresponding to the selected pressure is visually identifiable when the cuff is secured snugly around the limb at the selected location, and wherein each pressure graduation is an estimate of the minimum constant pressure in the tube which will normally occlude blood flow over a time period suitably long for the performance of a surgical procedure when the cuff is secured snugly around a normal limb of predetermined circumference in a normotensive subject.

2. An occlusive cuff for safely occluding blood flow into a portion of a limb as small as a single, isolated digit to facilitate surgery, comprising in combination:
   (a) an inflatable, readily collapsible tube of thin, flexible and substantially inextensible material having a length sufficient to encircle the limb, wherein the ratio of tube width to the circumference of the limb is substantially different than the ratio of tube width to limb circumference required in a sphygmomanometer cuff for accurate estimation of blood pressure in the limb;
   (b) tube-securing means for securing the tube around a limb having any circumference within a predefined range in a manner such that the tube substantially encircles the limb without overlapping on itself around the limb;
   (c) a retaining strap for wrapping around the outer surface of the collapsed tube encircling the limb to direct inflation inwardly when the tube is pressurized; and
   (d) strap-securing means for securing the strap around the outer surface of the tube as it encircles the limb wherein the strap-securing means secures the strap independently of the tube-securing means such that the tube remains encircling the limb if either the tube-securing means or the strap-securing means becomes ineffective.

3. An occlusive cuff for safely occluding blood flow into a portion of a limb as small as a single, isolated digit to facilitate surgery, comprisintg in combination:
   (a) an inflatable, readily collapsible tube of thin, flexible and substantially inextensible material having a length sufficient to encircle the limb, wherein the ratio of tube to the circumference of the limb is substantially different than the ratio of the tube width to limb circumference required in a sphygmomanometer cuff for accurate estimation of blood pressure in the limb;
   (b) tube-securing means for securing the tube around a limb having any circumference within a predefined range in a manner such that the tube substantially encircles the limb without overlapping on itself around the limb;
   (c) pressurizing means coupled to one end of the tube for supplying gas near a selected pressure to the tube for the duration of a surgical procedure; and
   (d) pressure sensing means for producing an indication representative of the pressure of gas in the tube for the duration of a surgical procedure, wherein the pressure sensing means is coupled to the opposite end of the tube such that there must be an opening in the tube around substantially all of the circumference of the limb encircled by the tube for the pressure sensing means to indicate the pressure of the gas supplied by the pressurizing means.

4. An occlusive cuff as defined in claim 3 wherein the tube-securing means includes means for enabling gas to flow within the portion of the tube in contact with the tube-securing means when the tube is secured around the limb.

5. An occlusive cuff for safely occluding blood flow into a portion of a limb to facilitate surgery on the limb portion, comprising in combination:
   (a) a pressurizable tube for positioning on a limb at a selected location;

(b) an occlusive band for encircling the limb and tube to secure the tube in position at the selected location on the limb and to direct inflation of the tube inwardly toward the limb when the tube is pressurized; and (c) occlusion pressure selection means for selecting remotely a constant pressure to which the secured tube should be pressurized, wherein the occlusion pressure selection means comprises pressure graduations marked on a surface of the occlusive band in a manner such that the pressure graduation corresponding to the selected pressure is visually indentifiable when the occlusive band is secured snugly around the limb, and wherein each pressure graduation is an estimate of the minimum constant pressure normally required in the tube when the tube is secured snugly on a non-hypertrophied and non-atrophied limb of predetermined circumference in a normotensive subject to occlude blood flow into the limb distal to the location over a time period suitably long for the performance of a surgical procedure.

6. An occlusive cuff as defined in claim 3 wherein the cuff pressure sensing means produces a cuff pressure signal representative of the pressure of gas in the tube and including:

(a) supply pressure sensing means for producing a supply pressure signal representative of the pressure of gas supplied to the tube, and (b) pressure comparison means for producing a differential signal representative of the difference between the cuff pressure signal and the supply pressure signal.

7. An occlusive cuff as defined in claim 6 including alarm means for producing a blockage alarm when the differential signal exceeds a predetermined limit.

8. An occlusive cuff system for safely occluding blood flow into a portion of a limb as small as a single, isolated digit to facilitate surgery distal to the cuff, comprising in combination:

(a) an inflatable, readily collapsible and substantially inextensible tube for placing on the surface of a portion of a limb with the longitudinal axis of the tube parallel to the longitudinal axis of the limb portion;

(b) an occlusive band for encircling a portion of the limb onto which the tube has been placed longitudinally;

(c) first pressurizing means for causing pressure to be applied to the limb portion and segment of the tube beneath the occlusive band;

(d) second pressurizing means for causing fluid at a variable pressure to be coupled to one end of the tube;

(e) pressure-sensing means for producing a signal representative of the pressure of the second pressurizing means; and (f) opening-pressure estimation means for varying the pressure of the second pressurizing means and for producing an opening pressure signal representative of the lowest pressure at which fluid passes from the end coupled to the second pressurizing means beneath the occlusive band to the other end of the tube.

9. An occlusive cuff system as defined in claim 8 including pressure-regulating means responsive to the opening pressure signal for regulating the first pressurizing means in a manner such that the opening pressure signal is maintained near a selected level.

10. An occlusive cuff system as defined in claim 8 wherein the width of the tube is sufficiently small relative to the circumference of the limb portion being encircled such that the tube conforms smoothly to the extremity beneath the occlusive band.

11. An occlusive cuff for encircling a digit and safely occluding blood flow into the digit of a human subject distal to the cuff for the duration of a surgical procedure, comprising in combination:

(a) a pressurizable, substantially inextensible tube having a length sufficient for encircling a digit at a selected location, and having a width wherein the ratio of the tube with to digit circumference at the selected location is substantially different than the ratio of bladder width to digit circumference required in a sphygmomanometer cuff for accurate estimation of blood pressure at the selected location;

(b) means for snugly encircling the digit with the tube at the selected location in a manner that does not allow the tube to contact the digit distal to the selected location, and so that the tube contacts the digit around substantially all of its circumference without overlapping around the digit;

(c) tube-securing means for securing the tube so that the tube remains snugly around the digit at the selected location while the tube is pressurized;

(d) pressurizing means for pressurizing the tube;

(e) pressure relief means for depressurizing the tube;

(f) pressure sensing means for producing a tube pressure output signal representative of the pressure to which the tube is pressurized;

(g) selectable reference signal means for producing any one of a number of constant signals, each representative of a predetermined constant reference pressure; and (h) pressure regulator means responsive to the tube pressure output signal for selectably activating the pressurizing means and the pressure relief means to maintain the tube pressure near a selected pressure over a time period suitably long for the performance of a surgical procedure.

12. An occlusive cuff comprising:

(a) a pressurizing band for encircling the limb of a subject having predetermined blood pressure and for applying pressure to the limb, wherein the length of the outer surface of the encircling band does not change substantially as pressure is applied to the limb; and (b) pressure graduations visible on the outer surface of the band for providing an estimate while pressure is not applied by the band of the minimum constant pressure which should normally be maintained by the band encircling the limb of the subject having predetermined blood pressure to occlude blood flow distal to the band for a desired time period.

13. An occlusive cuff system comprising:

(a) a pressurizing band for encircling the limb of a subject and for applying pressure to the limb;

(b) means for measuring the subject's systolic blood pressure; and (c) pressure graduations visible on the encircling band for indicating the level of the pressure applied by the band in relation to the subject's measured systolic blood pressure so that the band occludes blood flow distal to the band.

* * * * *